United States Patent
Watanabe et al.

(10) Patent No.: US 10,863,917 B2
(45) Date of Patent: Dec. 15, 2020

(54) EXCITEMENT PROPAGATION VISUALIZATION APPARATUS AND EXCITEMENT PROPAGATION VISUALIZATION METHOD

(71) Applicants: FUJITSU LIMITED, Kawasaki (JP); The University of Tokyo, Bunkyo-Tokyo (JP)

(72) Inventors: Masahiro Watanabe, Kawasaki (JP); Toshiaki Hisada, Kashiwa (JP); Seiryo Sugiura, Bunkyo (JP); Jun-ichi Okada, Bunkyo (JP); Takumi Washio, Bunkyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/157,585

(22) Filed: Oct. 11, 2018

(65) Prior Publication Data
US 2019/0110706 A1    Apr. 18, 2019

(30) Foreign Application Priority Data
Oct. 17, 2017  (JP) ................. 2017-200934

(51) Int. Cl.
*A61B 5/044* (2006.01)
*A61B 5/0432* (2006.01)
(Continued)

(52) U.S. Cl.
CPC .......... *A61B 5/044* (2013.01); *A61B 5/04011* (2013.01); *A61B 5/04021* (2013.01);
(Continued)

(58) Field of Classification Search
None
See application file for complete search history.

(56) References Cited

U.S. PATENT DOCUMENTS

| 4,745,550 A * | 5/1988 | Witkin ............... G01V 1/32 382/109 |
| 5,038,791 A * | 8/1991 | Collins ............... A61B 5/0402 600/509 |

(Continued)

OTHER PUBLICATIONS

Baxter et al, "Visualizing Excitation Waves inside Cardiac Muscle Using Transillumination", Biophysical Journal, vol. 80, pp. 516-530, Jan. 2001. (Year: 2001).*

(Continued)

*Primary Examiner* — Patrick F Valdez
(74) *Attorney, Agent, or Firm* — Xsensus LLP

(57) ABSTRACT

An excitement propagation visualization apparatus detects an excitement propagation wave front for each analysis time on the basis of excitement propagation data indicative of a potential generated by excitement propagation. Next, the excitement propagation visualization apparatus detects for each analysis time an intersection of a straight line passing through a first point inside a heart and a second point outside the heart and the excitement propagation wave front. Furthermore, the excitement propagation visualization apparatus generates for each analysis time a display object associated with the intersection of the straight line and the excitement propagation wave front. In addition, the excitement propagation visualization apparatus draws the display object generated for each analysis time at a position of the associated intersection in a drawing area indicative of an analysis space.

3 Claims, 15 Drawing Sheets

(51) Int. Cl.
  *G06T 11/20* (2006.01)
  *A61B 5/04* (2006.01)
  *A61B 5/0402* (2006.01)
  *G16H 50/50* (2018.01)

(52) U.S. Cl.
  CPC .......... *A61B 5/0432* (2013.01); *G06T 11/206* (2013.01); *G16H 50/50* (2018.01); *A61B 5/04028* (2013.01); *G06T 2210/41* (2013.01)

(56) References Cited

U.S. PATENT DOCUMENTS

| | | | |
|---|---|---|---|
| 6,187,032 B1* | 2/2001 | Ohyu ................ | A61B 5/04007 600/409 |
| 2003/0149354 A1 | 8/2003 | Bakharev | |
| 2015/0348310 A1* | 12/2015 | Watanabe ............ | G06T 7/0014 345/420 |
| 2017/0185740 A1* | 6/2017 | Seegerer ................ | G16H 50/50 |

OTHER PUBLICATIONS

Extended European Search Report dated Mar. 15, 2019 issued in corresponding European Application No. 18198182.0, 8 pages.
Alday, E, et al., "Comparison of Electric- and Magnetic-Cardiograms Produced by Myocardial Ischemia in Models of the Human Ventricle and Torso," PLOS ONE 11(8): e0160999. doi:10. 1371/ joumal.pone.0160999, 2016, pp. 17.

* cited by examiner

EXCITEMENT PROPAGATION VISUALIZATION APPARATUS AND EXCITEMENT PROPAGATION VISUALIZATION METHOD

CROSS-REFERENCE TO RELATED APPLICATION

This application is based upon and claims the benefit of priority of the prior Japanese Patent Application No. 2017-200934, filed on Oct. 17, 2017, the entire contents of which are incorporated herein by reference.

FIELD

The embodiments discussed herein are related to an excitement propagation visualization apparatus and an excitement propagation visualization method.

BACKGROUND

In recent years heart simulation techniques which reproduce the motion of a heart by the use of a computer have developed. The use of a heart simulation makes it possible to grasp in detail the state of a patient having a heart disease from outside the body without performing a surgical operation. For example, the state of the myocardial behavior or ischemia of the patient is reproduced by doing a heart simulation. Furthermore, by doing a simulation which reproduces the state of excitement propagation in the heart, an electrocardiogram of the patient is obtained accurately by the use of a virtual chest on which the patient's chest is reproduced. Excitement propagation is a propagation of an electrical impulse which occurs at the sinoatrial node or atrioventricular node of a heart and propagates to myocardia and surrounding tissues.

For example, a method of displaying times by the use of an isopleth map obtained by connecting positions at which an R wave arrives at a body surface at the same time is known as a method for indicating the state of excitement propagation. Furthermore, a method of displaying potentials of a body surface at a given time by the use of an isopleth map is known.

U.S. Patent Application Publication No. 2003/0149354

Erick A. Perez Alday, Haibo Ni, Chen Zhang, Michael A. Colman, Zizhao Gan, Henggui Zhang, "Comparison of Electric- and Magnetic-Cardiograms Produced by Myocardial Ischemia in Models of the Human Ventricle and Torso", PLOS ONE, DOI:10.1371/journal.pone.0160999, Aug. 24, 2016

If the state of excitement propagation is reproduced in detail by doing a heart simulation, the state of a patient which an electrocardiogram does not indicate may be grasped. For example, the influence of a heart disease which does not appear in an electrocardiogram may appear in the state of excitement propagation in a body.

However, even if the state of excitement propagation in a body is reproduced by doing a heart simulation, there are no means of plainly visualizing the state.

SUMMARY

According to an aspect, there is provided an excitement propagation visualization apparatus including: a memory that stores excitement propagation data indicative of potentials generated by excitement propagation at a plurality of points in an analysis space including a heart at each analysis time in an analysis period; and a processor that detects, based on the excitement propagation data and for each analysis time, an excitement propagation wave front indicative of a boundary between an area in which the potentials exceed a threshold and an area in which the potentials do not exceed the threshold, that detects, for each analysis time, an intersection of a straight line passing through a first point inside the heart and a second point outside the heart and the excitement propagation wave front, that generates, for each analysis time, a display object associated with the intersection of the straight line and the excitement propagation wave front, and that draws the display object generated for each analysis time at a position of the associated intersection in a drawing area indicative of the analysis space.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Embodiments will now be described with reference to the accompanying drawings. As long as there is no inconsistency, a plurality of embodiments may be combined.

First Embodiment

First a first embodiment will be described.

Figure 1:
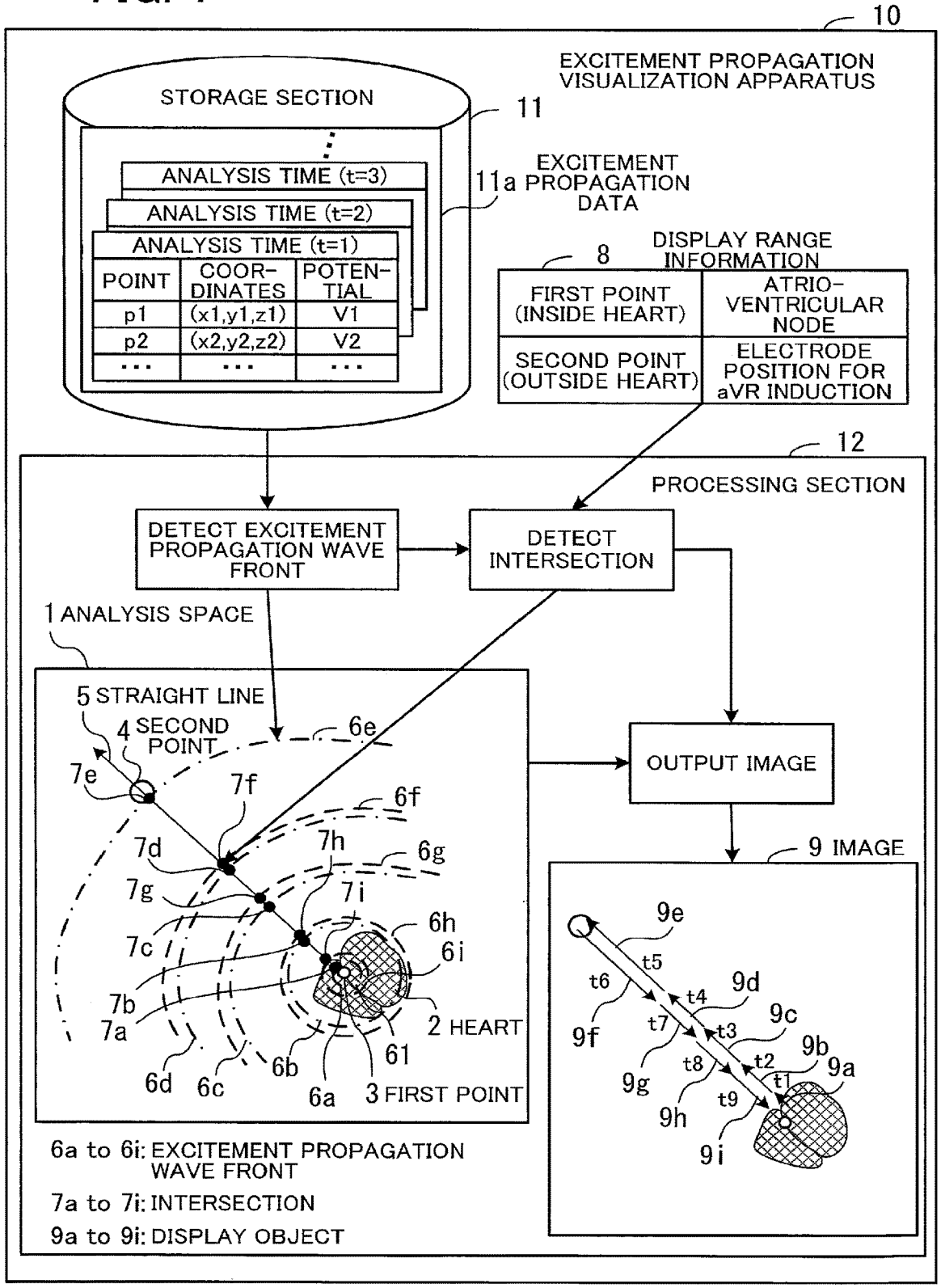
FIG. 1 illustrates an example of an excitement propagation visualization apparatus according to a first embodiment.

FIG. 1 illustrates an example of an excitement propagation visualization apparatus according to a first embodiment. An excitement propagation visualization apparatus 10 includes a storage section 11 and a processing section 12. For example, the storage section 11 is a memory or a storage unit included in the excitement propagation visualization apparatus 10. For example, the processing section 12 is a processor or a processing element included in the excitement propagation visualization apparatus 10.

The storage section 11 stores excitement propagation data 11a indicative of potentials generated by excitement propagation at a plurality of points in an analysis space 1 including a heart 2 at each of a plurality of analysis times in an analysis period. For example, the excitement propagation data 11a are obtained by reproducing excitement propagation in the heart 2 by an excitement propagation simulation which is a kind of computer simulation. The analysis times are set at determined time intervals in the analysis period on the excitement propagation simulation. Time on the simulation progresses in a process (time step). For example, an analysis time is represented by the number of a time step.

For example, when display range information 8 is inputted, the processing section 12 outputs an image 9 indicative of the state of excitement propagation in accordance with the display range information 8. A first point 3 and a second point 4 are designated in the display range information 8 as the both ends of a range to be displayed. The first point 3 is inside the heart 2. For example, the position of a sinoatrial node or an atrioventricular node is designated as the first point 3. The second point 4 is outside the heart 2. For example, one of electrode positions at the time of measuring an electrocardiogram is designated as the second point 4. For example, the display range information 8 is inputted by a user who confirms the state of excitement propagation according to a part in which the user wants to confirm the state.

Excitement propagation wave fronts 6a through 6i indicative of a boundary between an area in which a potential exceeds a threshold and an area in which a potential does not exceed the threshold are detected for each of the plurality of analysis times on the basis of the excitement propagation data 11a. The threshold is designated in advance by the user. For example, if the position of a sinoatrial node is designated as the first point 3, then the user designates as the threshold a value obtained by subtracting a constant value set by assuming the attenuation of a P wave on an electrocardiogram. Furthermore, if the position of an atrioventricular node is designated as the first point 3, then the user designates as the threshold a value obtained by subtracting a constant value set by assuming the attenuation of an R wave on an electrocardiogram.

If there is more than one boundary for one analysis time between an area in which a potential exceeds the threshold and an area in which a potential does not exceed the threshold (boundary in the direction in which a wave travels and a boundary in the opposite direction), then the processing section 12 considers as an excitement propagation wave front a surface indicative of a boundary more distant from the heart 2.

Next, the processing section 12 detects intersections 7a through 7i of a straight line 5 passing through the first point 3 inside the heart 2 and the second point 4 outside the heart 2 and the excitement propagation wave fronts 6a through 6i, respectively, for the plurality of analysis times.

Next, the processing section 12 generates display objects 9a through 9i associated with the intersections 7a through 7i of the straight line 5 and the excitement propagation wave fronts 6a through 6i, respectively, for the plurality of analysis times. For example, each of the display objects 9a through 9i indicates the direction in which an excitement propagation wave front travels and the speed at which the excitement propagation wave front travels. Each of the display objects 9a through 9i is a vector, for example, where the direction from the first point 3 to the second point 4 is positive (+) and the opposite direction is negative (−). In this case, for example, the processing section 12 finds a vector indicative of the direction and speed of excitement propagation at a position on each of the excitement propagation wave fronts 6a through 6i nearest the straight line 5. Specifically, to generate a display object for a first analysis time, the processing section considers an intersection detected for a second analysis time, which is immediately before the first analysis time, as a starting point of a vector to be generated. Furthermore, the processing section 12 considers an intersection detected for the first analysis time as an end point of the vector to be generated. In addition, the processing section 12 generates the display object which is an arrow (vector) indicating the direction from the starting point to the end point.

The processing section 12 outputs an image 9 on which the display objects 9a through 9i for the plurality of analysis times are drawn at the positions of the corresponding intersections 7a through 7i in a drawing area indicative of the analysis space 1. For example, to generate display objects which are arrows, the processing section 12 draws the display objects such that the end points of the arrows are placed at the positions of the corresponding intersections 7a through 7i.

The state of excitement propagation for the plurality of analysis times is plainly indicated in this way by the use of the image 9. That is to say, a three-dimensional propagation process is confirmed, for example, as positions for the plurality of analysis times on the straight line 5, which connects the atrioventricular node and an electrode, by excitement propagation wave fronts in the heart and chest. For example, the direction of excitement propagation is indicated by the direction of an arrow. As a result, it becomes clear to which direction an excitement propagation wave front travels at each analysis time, to an endocardium, to an epicardium, or to a body surface. Furthermore, the position of an excitement propagation wave front at each analysis time is indicated by the position of a display object. As a result, for example, to which part an excitement propagation wave front has reached at each analysis time is plainly displayed.

In addition, an object of display is limited to the state of excitement propagation on the straight line 5. Therefore, even if the state of excitement propagation for a plurality of analysis times is displayed on the image 9, the number of objects displayed on the image 9 is small. As a result, the state of excitement propagation for each analysis time is easily recognized.

Furthermore, the display is not a dynamic image or a plurality of images that are displayed by switching one after another, but it is the one image 9 that illustrates the state of excitement propagation for a plurality of analysis times. As a result, the state of excitement propagation for a specific patient is confirmed at a glance. This is very convenient in a case where a comparison is made between multiple states of excitement propagation. For example, there is a case where a comparison is made between the states of excitement propagation for a plurality of patients.

The processing section 12 may generate as the display objects 9a through 9i display objects indicative of portions of the excitement propagation wave fronts 6a through 6i included in a pillar-shaped area surrounding the straight line 5. In this case, the processing section 12 outputs an image 9 in which the display objects for a plurality of analysis times are drawn in the pillar-shaped area. By displaying the display objects 9a through 9i in this way in the pillar-shaped area, the state in which the excitement propagation wave fronts travel is easily grasped by the positions of the display objects 9a through 9i displayed in the pillar-shaped area.

Furthermore, the processing section 12 may generate as the display objects 9a through 9i display objects indicative of portions of the excitement propagation wave fronts 6a through 6i included in a pillar-shaped area surrounding the straight line 5. In this case, the processing section 12 outputs an image 9 in which display objects generated for one pulsation period are drawn in a ring-shaped area obtained by transforming the pillar-shaped area. By displaying the display objects 9a through 9i in this way in the ring-shaped area, the state in which the excitement propagation wave fronts travel during one pulsation period is easily grasped by the positions of the display objects 9a through 9i displayed in the ring-shaped area.

Second Embodiment

Next, a second embodiment will be described. In a second embodiment, a change in excitement propagation wave fronts caused by the progress of time is plainly displayed by vector representation using an arrow.

Figure 2:
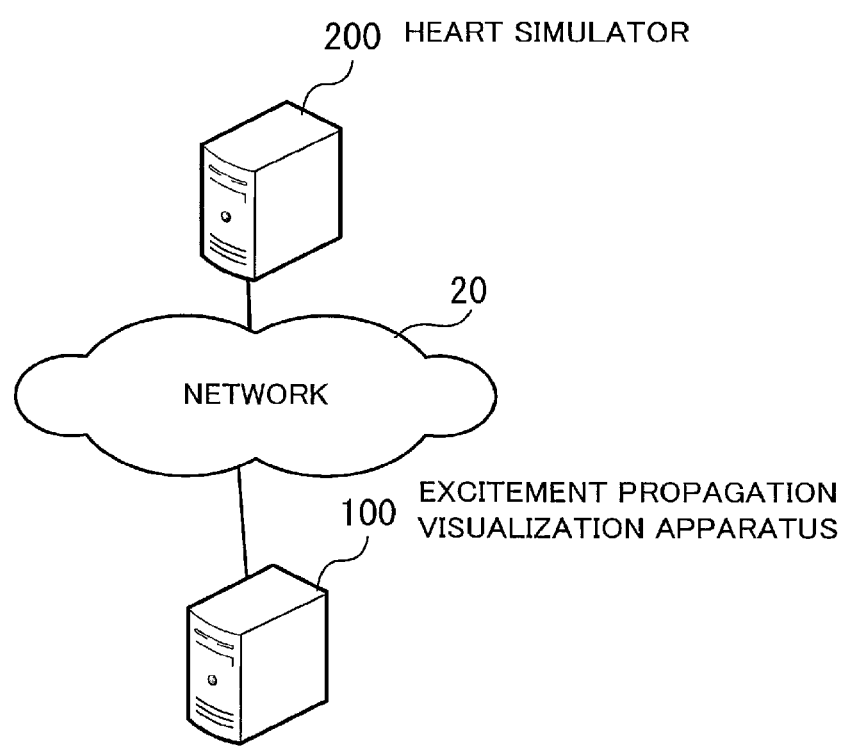
FIG. 2 illustrates an example of a system configuration in a second embodiment.

FIG. 2 illustrates an example of a system configuration in a second embodiment. In the example of FIG. 2, an excitement propagation visualization apparatus 100 is connected to a heart simulator 200 via a network 20. The heart simulator 200 is a computer which reproduces the motion of the heart of a patient by a simulation. For example, the heart simulator 200 uses a heart model reproduced from the heart of a specific patient for reproducing a time-series change in excitement propagation in the heart by a simulation. The heart simulator 200 generates excitement propagation data as a result of the simulation.

The excitement propagation visualization apparatus 100 is a computer which visualizes the state of excitement propagation. For example, the excitement propagation visualization apparatus 100 acquires from the heart simulator 200 excitement propagation data indicative of simulation results of excitement propagation. Furthermore, the excitement propagation visualization apparatus 100 displays the state of excitement propagation indicated by the acquired excitement propagation data in a form comprehensible to a user such as a doctor.

Figure 3:
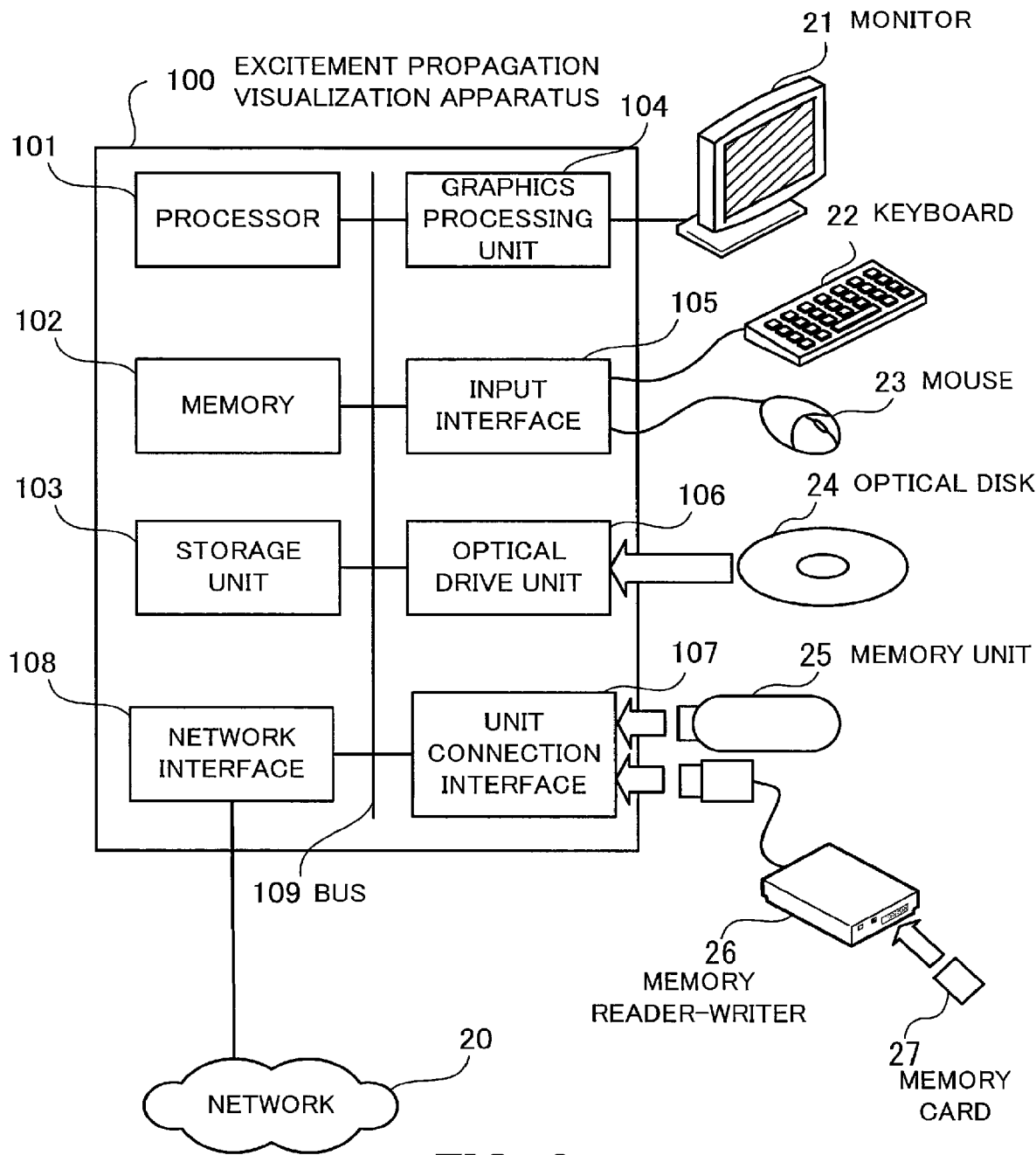
FIG. 3 illustrates an example of a hardware configuration of an excitement propagation visualization apparatus.

FIG. 3 illustrates an example of a hardware configuration of the excitement propagation visualization apparatus. The whole of the excitement propagation visualization apparatus 100 is controlled by a processor 101. A memory 102 and a plurality of peripheral units are connected to the processor 101 via a bus 109. The processor 101 may be a multiprocessor. The processor 101 is a central processing unit (CPU), a micro processing unit (MPU), a digital signal processor (DSP), or the like. At least part of functions which the processor 101 realizes by executing programs may be realized by an electronic circuit such as an application specific integrated circuit (ASIC) and a programmable logic device (PLD).

The memory 102 is used as main storage of the excitement propagation visualization apparatus 100. The memory 102 temporarily stores at least part of an operating system (OS) program or an application program executed by the processor 101. In addition, the memory 102 stores various pieces of data which the processor 101 uses for performing a process. A volatile semiconductor memory, such as a random access memory (RAM), is used as the memory 102.

The plurality of peripheral units connected to the bus 109 are a storage unit 103, a graphics processing unit 104, an input interface 105, an optical drive unit 106, a unit connection interface 107, and a network interface 108.

The storage unit 103 electrically or magnetically writes data to and reads out data from a built-in record medium. The storage unit 103 is used as auxiliary storage of the excitement propagation visualization apparatus 100. The storage unit 103 stores the OS program, application programs, and various pieces of data. A hard disk drive (HDD), a solid state drive (SSD), or the like is used as the storage unit 103.

A monitor 21 is connected to the graphics processing unit 104. The graphics processing unit 104 displays an image on a screen of the monitor 21 in accordance with an instruction from the processor 101. The monitor 21 is a display unit using a liquid crystal display (LCD) or the like.

A keyboard 22 and a mouse 23 are connected to the input interface 105. The input interface 105 transmits to the processor 101 signals transmitted from the keyboard 22 and the mouse 23. The mouse 23 is an example of a pointing device and another pointing device, such as a touch panel, a tablet, a touch pad, and a track ball, may be used.

The optical drive unit 106 reads data recorded on an optical disk 24 by the use of a laser beam or the like. The optical disk 24 is a portable record medium on which recorded data can be read by the reflection of light. The optical disk 24 is a digital versatile disc (DVD), a DVD-RAM, a compact disc read only memory (CD-ROM), a CD-recordable (R)/rewritable (RW), or the like.

The unit connection interface 107 is a communication interface used for connecting peripheral units to the excitement propagation visualization apparatus 100. For example, a memory unit 25 and a memory reader-writer 26 are connected to the unit connection interface 107. The memory unit 25 is a record medium having the function of communicating with the unit connection interface 107. The memory reader-writer 26 is a unit which writes data to or reads out data from a memory card 27. The memory card 27 is a card-type record medium.

The network interface 108 is connected to the network 20. The network interface 108 transmits data to or receives data from another computer or a communication apparatus via the network 20.

By adopting the above hardware configuration, the processing functions in the second embodiment are realized. The excitement propagation visualization apparatus 10 according to the first embodiment is also realized by adopting the same hardware that makes up the excitement propagation visualization apparatus 100 illustrated in FIG. 3.

The excitement propagation visualization apparatus 100 realizes the processing functions in the second embodiment by executing a program recorded in, for example, a computer-readable record medium. The program in which the contents of a process that is to be performed by the excitement propagation visualization apparatus 100 are described may be recorded in various record media. For example, the program which is to be executed by the excitement propagation visualization apparatus 100 is stored in the storage unit 103. The processor 101 loads at least part of the program stored in the storage unit 103 into the memory 102 and executes it. Furthermore, the program which is to be executed by the excitement propagation visualization apparatus 100 may be recorded on a portable record medium, such as the optical disk 24, the memory unit 25, and the memory card 27. The program recorded on the portable record medium is installed in the storage unit 103 to be executed under the control of the processor 101, for example. In addition, the processor 101 may read out the program directly from the portable record medium and execute it.

Figure 4:
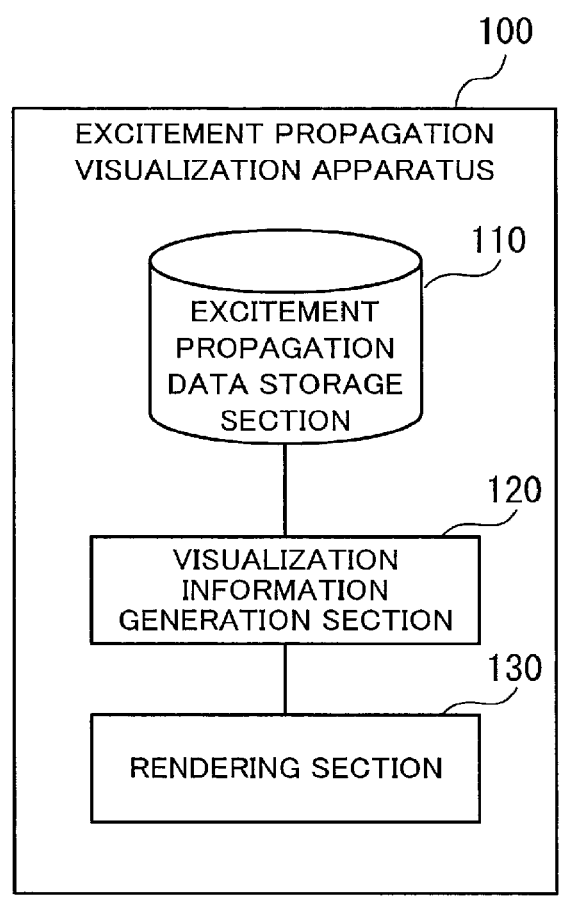
FIG. 4 is a block diagram illustrative of the functions of the excitement propagation visualization apparatus.

FIG. 4 is a block diagram illustrative of the functions of the excitement propagation visualization apparatus. The excitement propagation visualization apparatus 100 includes an excitement propagation data storage section 110, a visualization information generation section 120, and a rendering section 130.

The excitement propagation data storage section 110 stores excitement propagation data obtained as the result of a simulation done by the heart simulator 200. On the basis of the excitement propagation data, the visualization information generation section 120 generates image information indicative of a time-series change in excitement propagation in a body. On the basis of the image information generated by the visualization information generation section 120, the rendering section 130 generates an image and causes the monitor 21 to display the generated image.

The function of each component illustrated in FIG. 4 is realized by, for example, causing a computer to execute a program module corresponding to the component.

Figure 5:
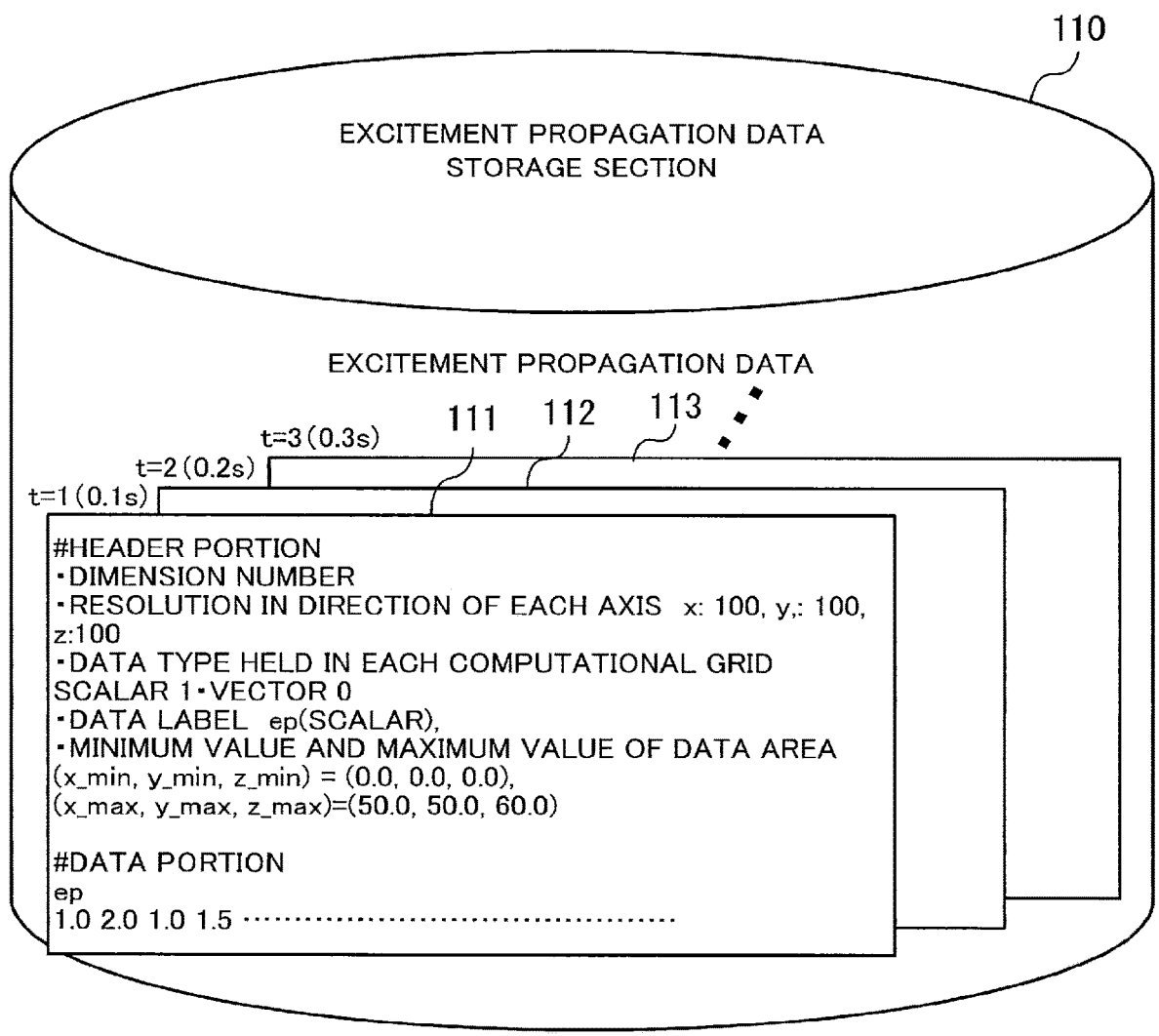
FIG. 5 illustrates an example of excitement propagation data.

FIG. 5 illustrates an example of excitement propagation data. The excitement propagation data storage section 110 stores excitement propagation data 111, 112, 113, and so on for individual time steps on a simulation. In the example of FIG. 5, the excitement propagation data 111, 112, 113, and so on indicate the state of excitement propagation for time steps that are set at intervals of 0.1 second and correspond to one cycle of pulsation. Time step numbers (t=1, 2, 3, and so on) are given to the excitement propagation data 111, 112, 113, and so on respectively.

The excitement propagation data 111, 112, 113, and so on each have a header portion and a data portion. A dimension number of an analysis area, resolution in the direction of each axis, a data type held in each computational grid, a data label, the minimum value (min) and maximum value (max) of a data area, and the like are included in the header portion. A potential at each grid point is set in the data portion. A potential in excitement propagation is an electromagnetic potential.

On the basis of the above excitement propagation data 111, 112, 113, and so on, the visualization information generation section 120 visualizes the state of excitement propagation on a straight line which connects two points in an area analyzed by an excitement propagation simulation. For example, the visualization information generation section 120 accepts from a user an input of two points to be used as reference points of a visualization target range. One point is selected from, for example, a sinoatrial node and an atrioventricular node. The other point is selected from, for example, electrode positions at the time of measuring an electrocardiogram.

Figure 6:
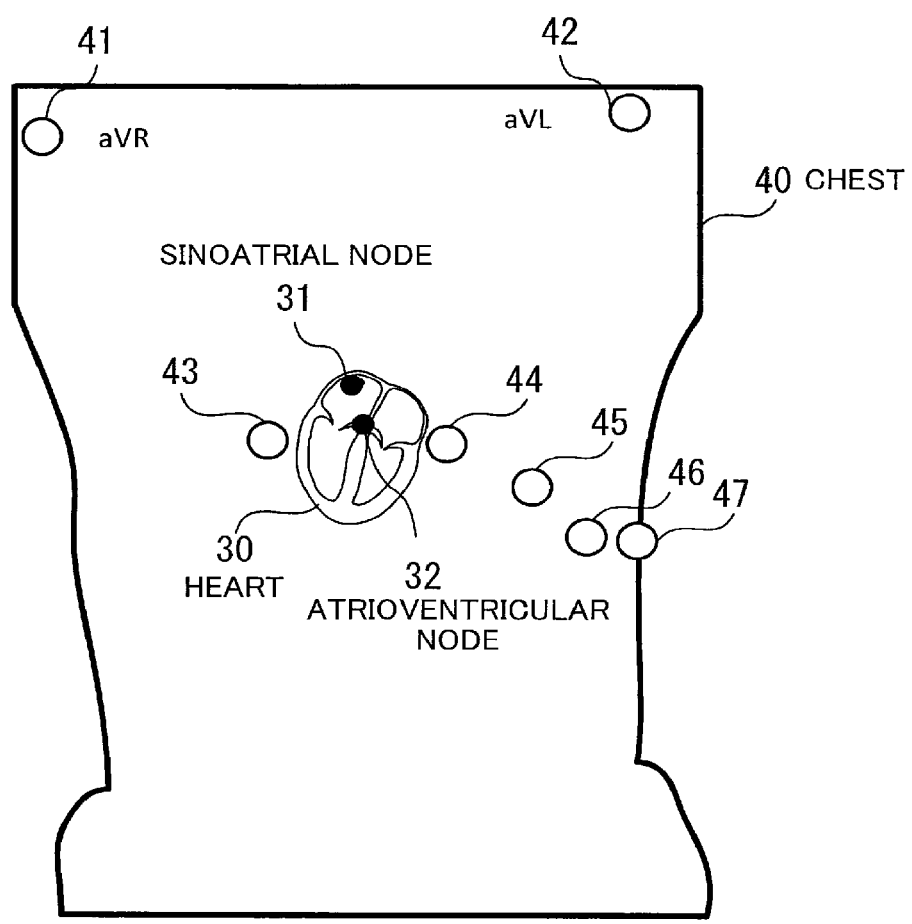
FIG. 6 illustrates an example of reference points of a visualization target range.

FIG. 6 illustrates an example of reference points of a visualization target range. In FIG. 6, a sinoatrial node 31 and an atrioventricular node 32 in a heart 30 and electrode positions 41 through 47 on a chest 40 are illustrated.

The heart 30 has the sinoatrial node 31 and the atrioventricular node 32 as important parts of an impulse conducting system. An impulse occurs first at the sinoatrial node 31 in the impulse conducting system. The impulse which occurs at the sinoatrial node 31 is conducted to an atrium and reaches the atrioventricular node 32. Furthermore, the atrioventricular node 32 which receives the impulse from the sinoatrial node 31 newly generates an impulse. That impulse is conducted to a ventricle.

An impulse propagating through the impulse conducting system is a change in potential. A myocardium which receives an impulse goes into an excited state and begins to contract. Therefore, excitement propagation is indicated by how an area in which a potential is higher than a determined value extends. A change in potential is observed by electrodes fitted on a body surface. A change in potential observed in this way is indicated by an electrocardiogram. The electrode positions 41 through 47 for making an electrocardiogram are determined in advance. Of the electrode positions 41 through 47, for example, the electrode position 41 on a right shoulder is for observing aVR induction. Furthermore, the electrode position 42 on a left shoulder is for observing aVL induction.

In order to visualize the state of excitement propagation, a user selects one of the sinoatrial node 31 and the atrioventricular node 32 as one reference point of a visualization target area. In addition, the user selects one of the electrode positions 41 through 47 used for making an electrocardiogram as the other reference point of the visualization target area. By selecting these reference points, excitement propagation to the one of the electrode positions 41 through 47 at the time of measuring an electrocardiogram is visualized.

For example, the visualization information generation section 120 generates an arrow object indicative of the state in which an excitement propagation wave front travels for each time step. That is to say, the visualization information generation section 120 finds a traveling vector on an excitement propagation wave front nearest a straight line passing through two points designated as the reference points for each time step. The direction in which an excitement propagation wave front travels is indicated by the direction of a traveling vector and the speed at which an excitement propagation wave front travels is indicated by the magnitude of a traveling vector. The visualization information generation section 120 generates an arrow object indicative of a traveling vector for each time step and transmits the arrow object to the rendering section 130 as an object of display.

Figure 7:
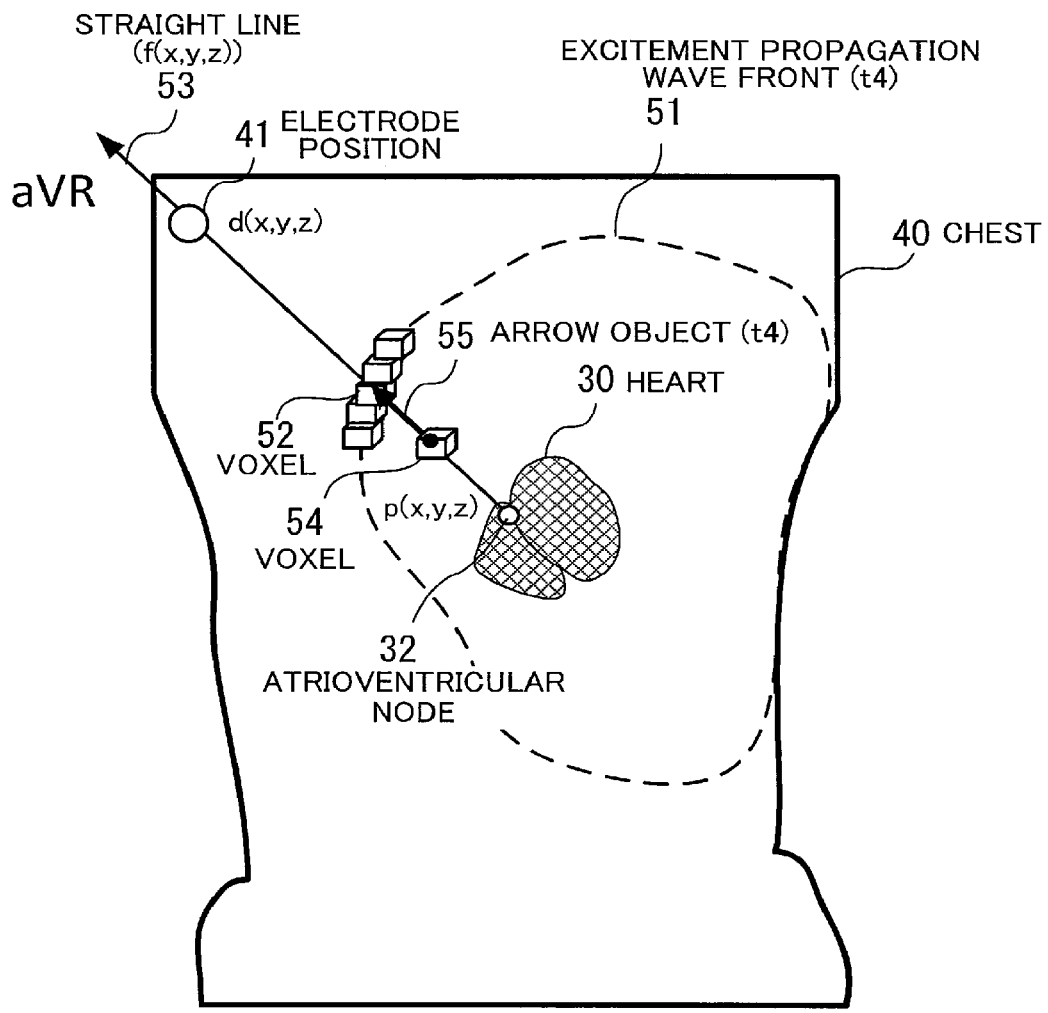
FIG. 7 illustrates an example of generating an arrow object.

FIG. 7 illustrates an example of generating an arrow object. In the example of FIG. 7, it is assumed that the atrioventricular node 32 and the electrode position 41 are designated as reference points. The coordinates of the atrioventricular node 32 are p(x, y, z) and the coordinates of the electrode position 41 are d(x, y, z). An example of generating an arrow object 55 indicative of the state in which an excitement propagation wave front 51 travels for a fourth time step (t=4) will now be described.

On the basis of excitement propagation data for the fourth time step, the visualization information generation section 120 extracts a voxel on the excitement propagation wave front 51. For example, a voxel having a potential which is in the range of a determined error with a threshold designated in advance is extracted as a voxel on the excitement propagation wave front 51. In addition, the visualization information generation section 120 generates a straight line 53 (f(x, y, z)) passing through the atrioventricular node 32 and the electrode position 41.

Furthermore, the visualization information generation section 120 specifies a voxel 52, from among voxels on the excitement propagation wave front 51, which intersects the straight line 53. In addition, the visualization information generation section 120 generates the arrow object 55 with a voxel 54 specified in the same way for the preceding time step (t=3) and a voxel 52 specified for the fourth time step as a starting point and an end point respectively.

By generating such an arrow object for each time step and displaying it on the monitor 21, the state of excitement propagation in a body for each time step is visualized.

A procedure for a visualization process of the state of excitement propagation will now be described in detail.

Figure 8:
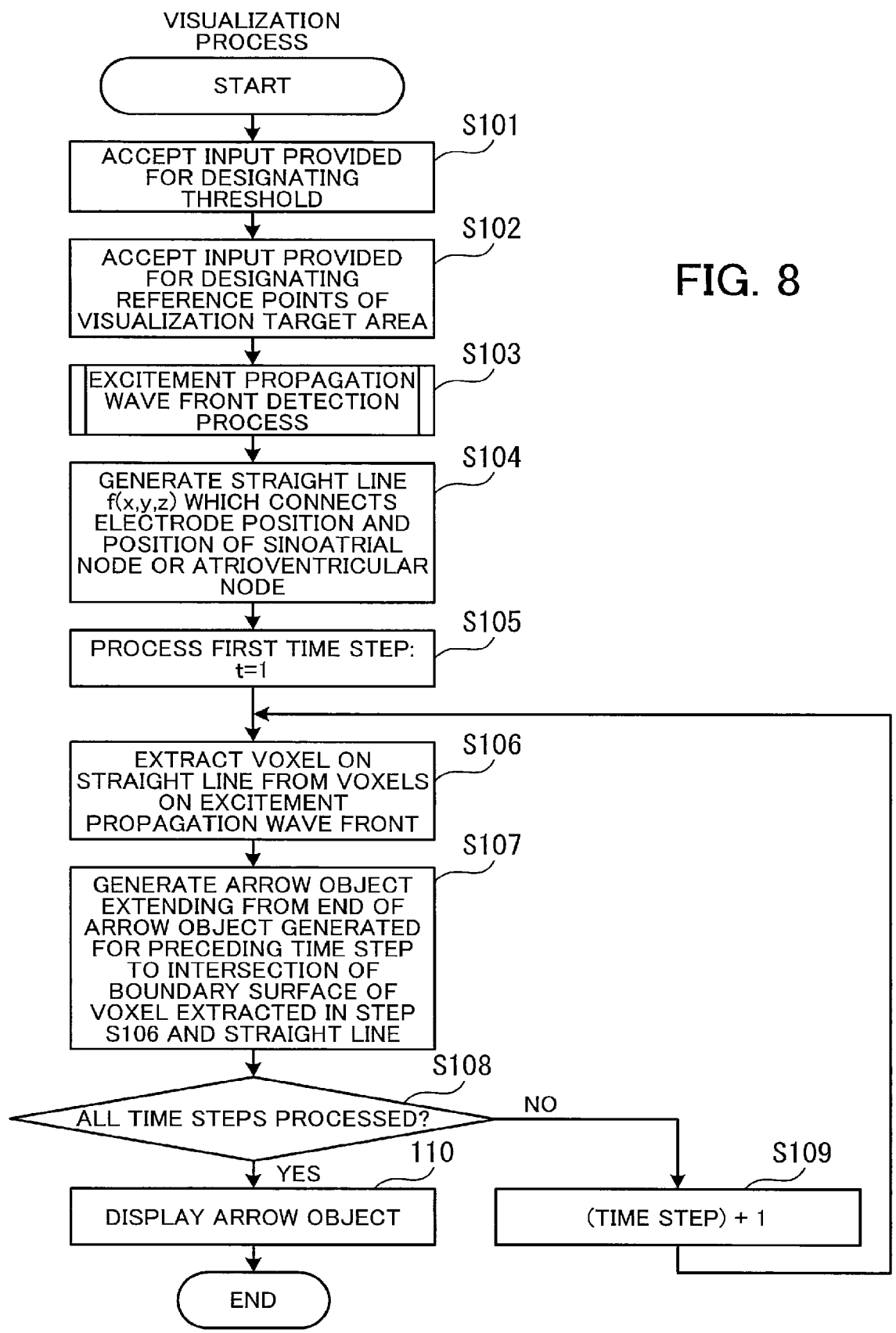
FIG. 8 is a flow chart illustrative of an example of a procedure for a visualization process.

FIG. 8 is a flow chart illustrative of an example of a procedure for a visualization process. The process illustrated in FIG. 8 will now be described in order of step number.

(Step S101) The visualization information generation section 120 accepts an input provided for designating a threshold of a potential on an excitement propagation wave front. An excitement propagation wave front is a boundary surface between an area in which a potential exceeds the threshold and an area in which a potential does not exceed the threshold, where a boundary surface more distant from the heart is taken as the excitement propagation wave front.

(Step S102) The visualization information generation section 120 accepts an input provided for designating reference points of a visualization target area. For example, the visualization information generation section 120 accepts an input provided for designating a total of two reference points. One reference point is one of the sinoatrial node 31 and the atrioventricular node 32 and the other reference point is one of the electrode positions 41 through 47.

(Step S103) The visualization information generation section 120 performs an excitement propagation wave front detection process. A voxel on an excitement propagation wave front is identified for each time step on an excitement propagation simulation by the excitement propagation wave front detection process. The details of the excitement propagation wave front detection process will be described later (see FIG. 9).

(Step S104) The visualization information generation section 120 generates a straight line f(x, y, z) which connects two reference positions (electrode position d(x, y, z) and a position p(x, y, z) of the sinoatrial node 31 or the atrioventricular node 32). The straight line f(x, y, z) is represented by a linear expression in three-dimensional space.

(Step S105) The visualization information generation section 120 processes a first time step (t=1).

(Step S106) The visualization information generation section 120 extracts a voxel on the straight line generated in step S104 from voxels on an excitement propagation wave front for a time step to be processed. For example, if a plurality of voxels are on the straight line generated in step S104, then the visualization information generation section 120 extracts a voxel more distant from the sinoatrial node 31 or the atrioventricular node 32.

(Step S107) The visualization information generation section 120 generates an arrow object extending from the end of an arrow object generated for the preceding time step to the intersection of the boundary surface of the voxel extracted in step S106 and the straight line. If a time step to be processed is the first time step, then the visualization information generation section 120 considers the position of the sinoatrial node or the atrioventricular node 32 designated as a reference position as a starting point of the arrow object. For example, the end point of the arrow object is one of the two intersections of the boundary surfaces of the above voxel and the straight line generated in step S104, where the one more distant from the sinoatrial node 31 or the atrioventricular node 32 is taken as the end point.

(Step S108) The visualization information generation section 120 determines whether or not all time steps have been processed. If there is a time step not yet processed, then the visualization information generation section 120 proceeds to step S109. If all the time steps have been processed, then the visualization information generation section 120 proceeds to step S110.

(Step S109) The visualization information generation section 120 considers the next time step as a time step to be processed (adds 1 to t). After that the visualization information generation section 120 performs step S106.

(Step S110) The rendering section 130 draws an image of an arrow object generated for each time step by superimposing it on an image of the heart or the chest. Furthermore, the rendering section 130 causes the monitor 21 to display the image obtained by the drawing. At this time, for example, the rendering section 130 causes the monitor 21 to display the number of each time step near the corresponding arrow object.

Next, the excitement propagation wave front detection process will be described in detail.

Figure 9:
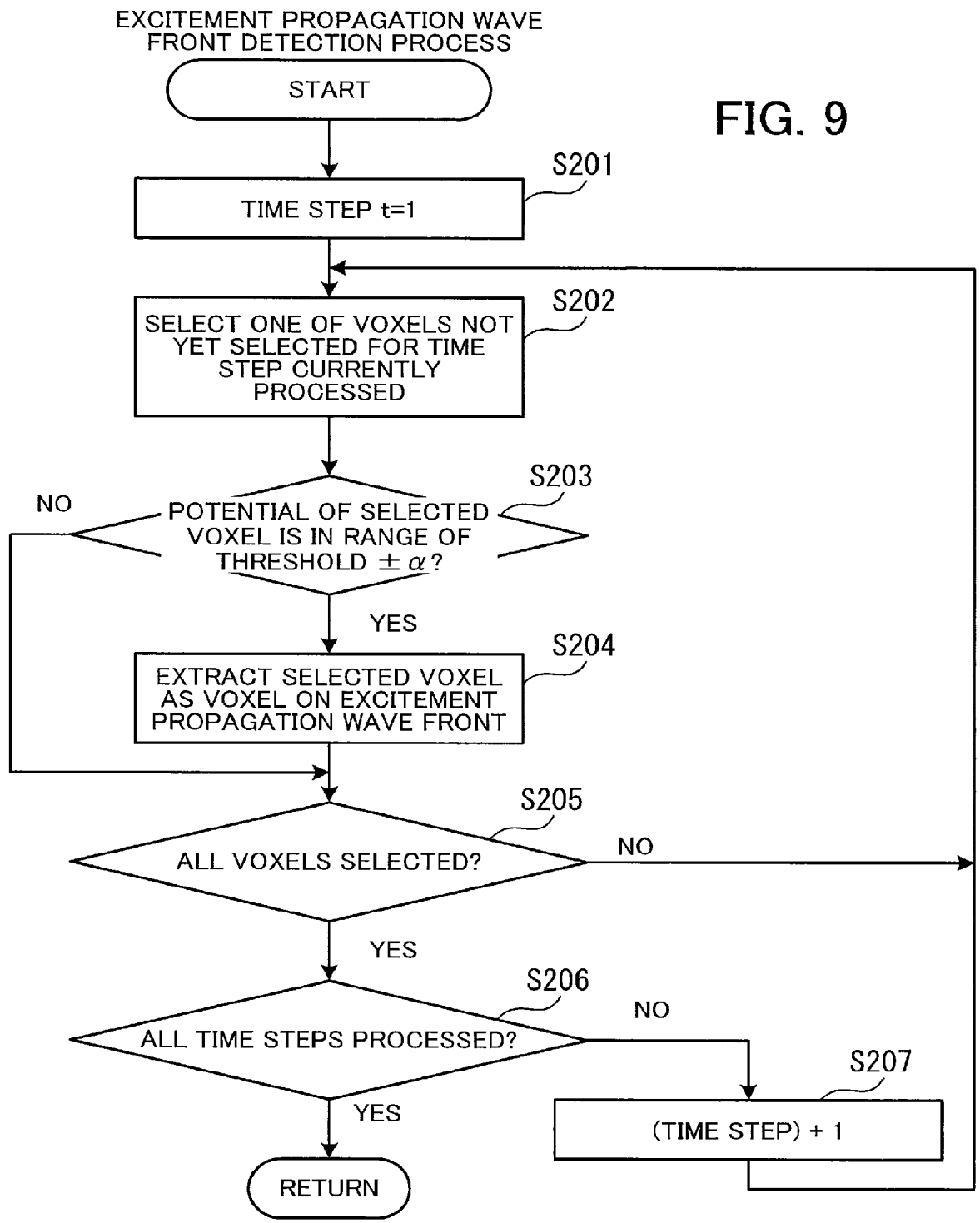
FIG. 9 is a flow chart illustrative of an example of a procedure for an excitement propagation wave front detection process.

FIG. 9 is a flow chart illustrative of an example of a procedure for the excitement propagation wave front detection process. The process illustrated in FIG. 9 will now be described in order of step number.

(Step S201) The visualization information generation section 120 processes a first time step (t=1).

(Step S202) The visualization information generation section 120 selects one of voxels not yet selected for the time step currently processed.

(Step S203) The visualization information generation section 120 determines whether or not a potential of the selected voxel is in the range of an error $\alpha$ ($\alpha$ is a positive real number) with the threshold. If the potential of the selected voxel is in the range of the error $\alpha$ from the threshold, then the visualization information generation section 120 proceeds to step S204. If the potential of the selected voxel is not in the range of the error $\alpha$ from the threshold, then the visualization information generation section 120 proceeds to step S205.

(Step S204) The visualization information generation section 120 extracts the selected voxel as a voxel on an excitement propagation wave front for the time step currently processed. For example, the visualization information generation section 120 associates the identifier of the selected voxel with the number of the time step currently processed and stores it in a memory.

(Step S205) The visualization information generation section 120 determines whether or not all voxels have been selected for the time step currently processed. If all the voxels have been selected for the time step currently processed, then the visualization information generation section 120 proceeds to step S206. If there is a voxel not yet selected for the time step currently processed, then the visualization information generation section 120 performs step S202.

(Step S206) The visualization information generation section 120 determines whether or not all time steps have been processed. If there is a time step not yet processed, then the visualization information generation section 120 proceeds to step S207. If all the time steps have been processed, then the visualization information generation section 120 ends the excitement propagation wave front detection process.

(Step S207) The visualization information generation section 120 considers the next time step as a time step to be processed (adds 1 to t). After that the visualization information generation section 120 performs step S202.

The state in which excitement propagation progresses for each time step is indicated in this way by an arrow object.

Figure 10:
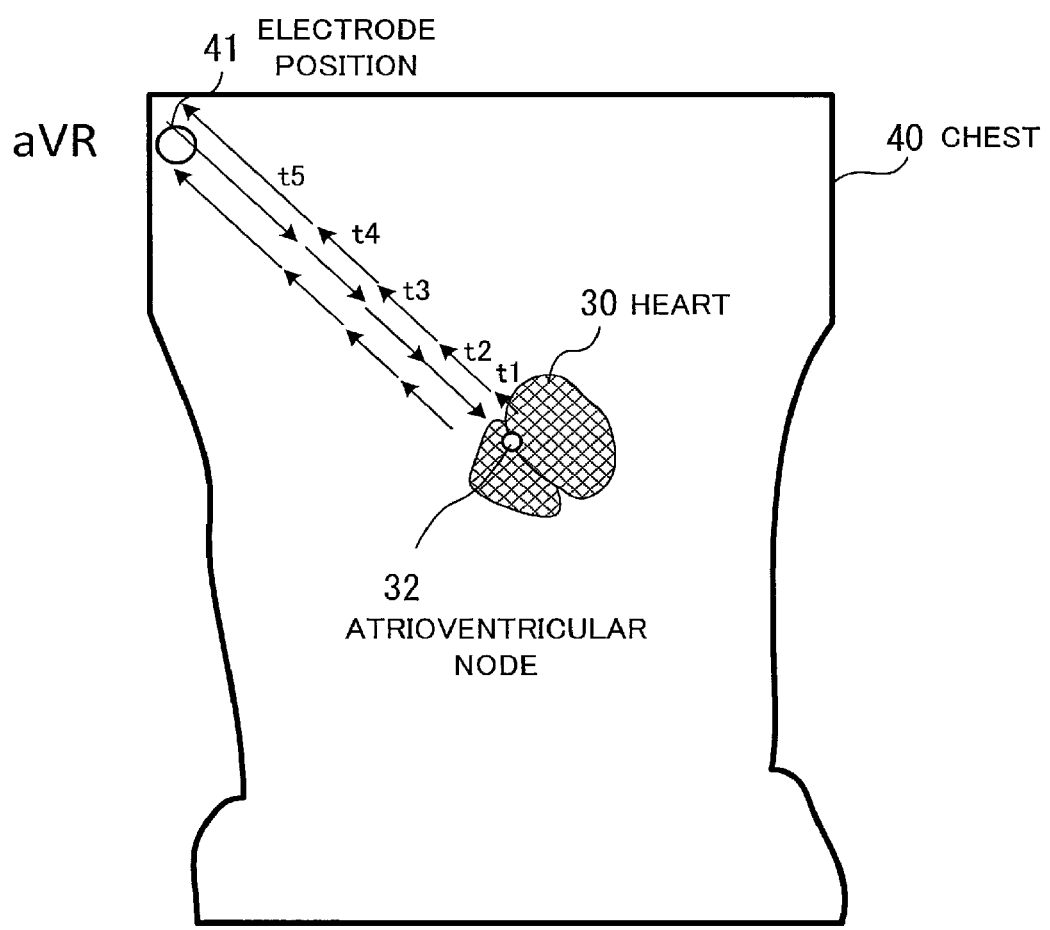
FIG. 10 illustrates an example of visualizing the state of excitement propagation by the use of arrow objects.

FIG. 10 illustrates an example of visualizing the state of excitement propagation by the use of arrow objects. In the example of FIG. 10, the state of excitement propagation from the atrioventricular node 32 to the electrode position 41 for observing aVR induction is indicated by an arrow object for each time step. With an arrow object indicative of the state in which excitement from the atrioventricular node 32 expands, an arrow indicates the direction to the electrode position 41. With an arrow object indicative of the process of excitement wearing off, an arrow indicates the direction to the atrioventricular node 32.

By indicating the state in which excitement propagation progresses for each time step by the use of an arrow object, the difference in the speed of excitement propagation at each time step is easily compared.

Furthermore, by comparing a change in potential at a specific part which appears in an electrocardiogram and the state of excitement propagation in a body indicated by an arrow object, the state of a patient is grasped more accurately.

Moreover, the excitement propagation visualization apparatus 100 may also display the state of excitement propagation in a body and an electrocardiogram measured at a designated electrode position side by side. By doing so, for example, the shape of a P wave or an R wave which appears in the electrocardiogram and the state in which the P wave or the R wave propagates in the body are compared and the state of the patient is grasped in detail. An electrocardiogram is reproduced from the excitement propagation data 111, 112, 113, and so on stored in the excitement propagation data storage section 110 on the basis of a potential value of a voxel corresponding to a designated electrode position.

Third Embodiment

Next, a third embodiment will be described. In a third embodiment, the state in which an excitement propagation wave front travels between two reference positions is displayed three-dimensionally in a pillar-shaped area. The differences between the third embodiment and the second embodiment will now be described.

Figure 11:
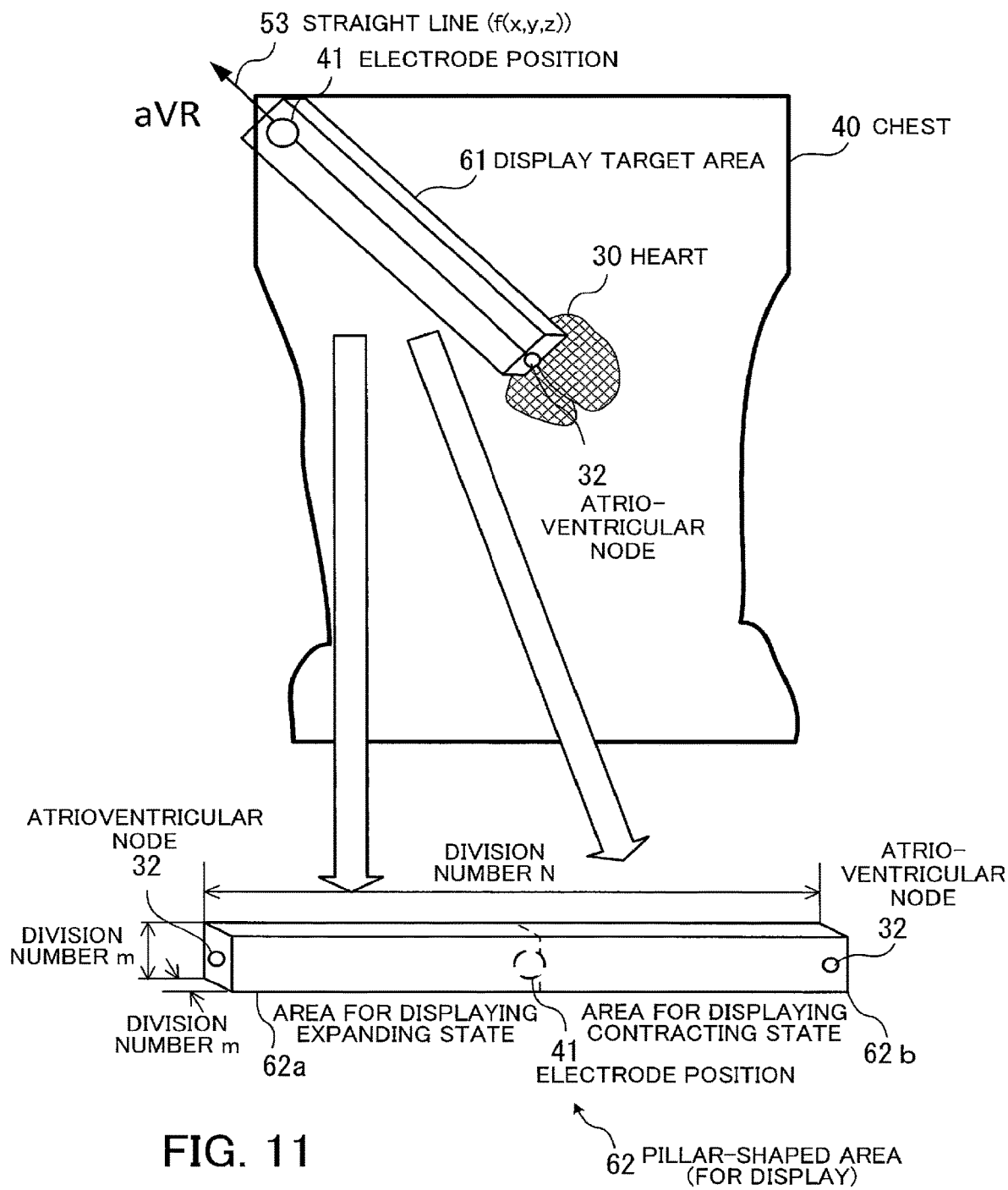
FIG. 11 illustrates an example of a pillar-shaped display target area in which the state of excitement propagation is displayed.

FIG. 11 illustrates an example of a pillar-shaped display target area in which the state of excitement propagation is displayed. The visualization information generation section 120 specifies a pillar-shaped display target area 61 from an analysis space on an excitement propagation simulation. In the example of FIG. 11, an area in the shape of a quadrangular prism in which a straight line 53 passing through an atrioventricular node 32 and an electrode position 41 is the central axis is specified as the display target area 61. The visualization information generation section 120 generates a pillar-shaped area 62 with a size of two display target areas 61, for display.

The pillar-shaped area 62 for display is divided into an area 62a in which the atrioventricular node 32 and the electrode position 41 are a starting point and an end point respectively and an area 62b in which the electrode position 41 and the atrioventricular node 32 are a starting point and an end point respectively. The area 62a is used for displaying the expanding state of an excitement propagation wave front, and the area 62b is used for displaying the contracting state of an excitement propagation wave front. The visualization information generation section 120 arranges in the area 62a an object indicative of an excitement propagation wave front in the display target area 61 for each time step when the excitement propagation wave front is expanding. In addition, the visualization information generation section 120 arranges in the area 62b an object indicative of an excitement propagation wave front in the display target area 61 for each time step when the excitement propagation wave front is contracting.

The visualization information generation section 120 arranges in the pillar-shaped area 62 a voxel on an excitement propagation wave front for each time step. By doing so, the visualization information generation section 120 generates an object indicative of an excitement propagation wave front. At this time the visualization information generation section 120 divides the pillar-shaped area 62 into a plurality of grids. For example, the visualization information generation section 120 divides the pillar-shaped area 62 by a determined division number n (n is an integer greater than or equal to 1) in the direction of an axis parallel to the direction in which an excitement propagation wave front travels, and divides the pillar-shaped area 62 by a determined division number m (m is an integer greater than or equal to 1) in the direction of an axis perpendicular to the direction in which an excitement propagation wave front travels. Furthermore, the visualization information generation section 120 sets at each grid point in the pillar-shaped area 62 a voxel on an excitement propagation wave front for any time step nearest the respective grid point. By doing so, a voxel on an excitement propagation wave front for each time step is arranged in the pillar-shaped area 62 and the arranged voxel forms an object indicative of the excitement propagation wave front.

Next, a procedure for a visualization process in the third embodiment will be described in detail.

Figure 12:
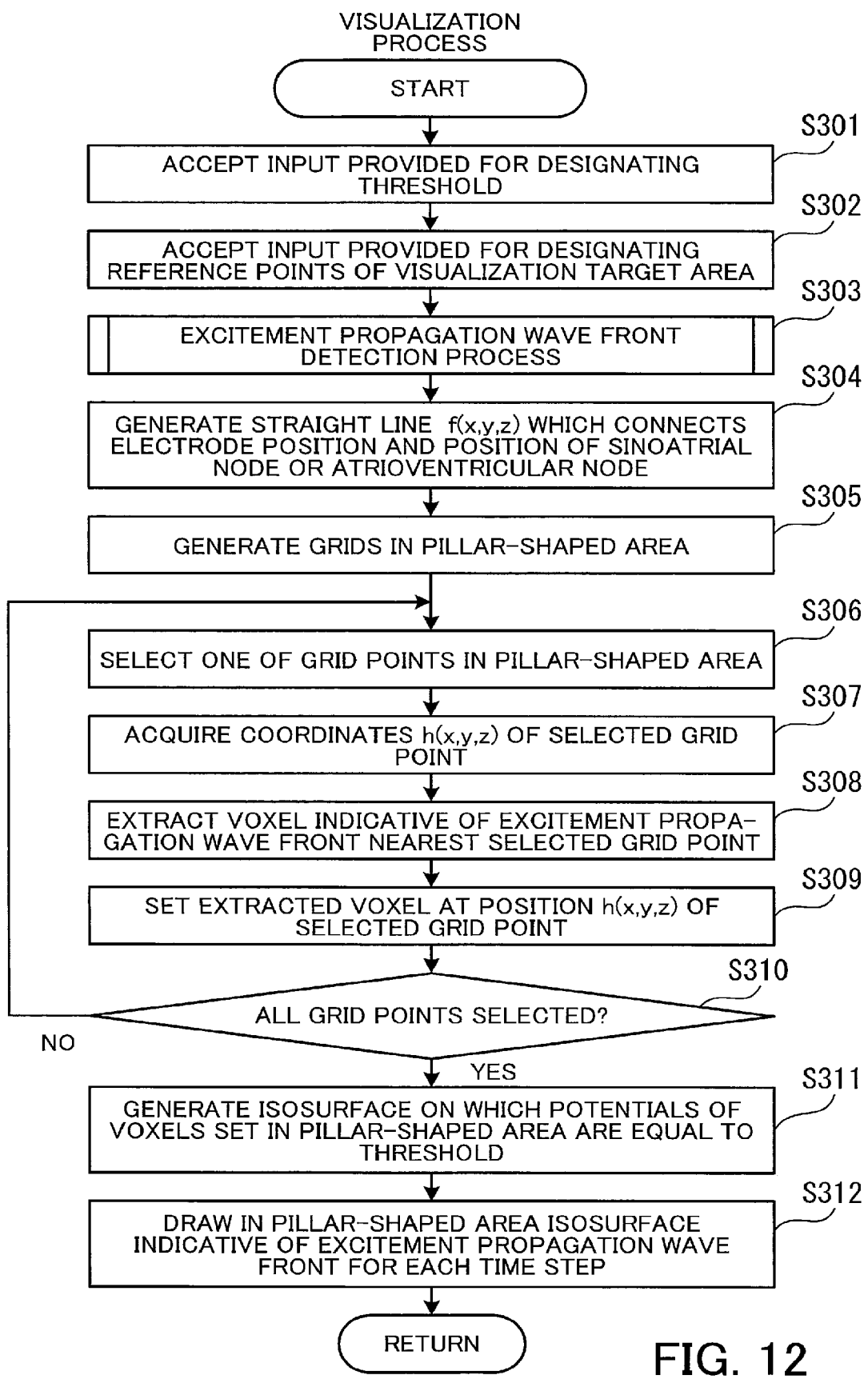
FIG. 12 is a flow chart illustrative of an example of a procedure for a visualization process in a third embodiment.

FIG. 12 is a flow chart illustrative of an example of a procedure for a visualization process in the third embodiment. Steps S301 through S304 are the same as steps S101 through S104, respectively, of the visualization process in the second embodiment illustrated in FIG. 8. Step S305 and the subsequent steps illustrated in FIG. 12 will now be described in order of step number.

(Step S305) The visualization information generation section 120 generates grids in a pillar-shaped area in which a line segment connecting an electrode position and an atrioventricular node or a sinoatrial node is the central axis.

(Step S306) The visualization information generation section 120 selects one of grid points in the pillar-shaped area.

(Step S307) The visualization information generation section 120 acquires coordinates h(x, y, z) of the selected grid point.

(Step S308) The visualization information generation section 120 extracts from voxels in a chest a voxel indicative of an excitement propagation wave front nearest the selected grid point. At this time the visualization information generation section 120 extracts only a voxel to which the distance from the selected grid point is shorter than a grid point interval ($\Delta x$, $\Delta y$, $\Delta z$).

(Step S309) The visualization information generation section 120 sets the extracted voxel at the position (coordinates h(x, y, z)) of the selected grid point in the pillar-shaped area.

(Step S310) The visualization information generation section 120 determines whether or not all the grid points have been selected. If all the grid points have been selected, then the visualization information generation section 120 proceeds to step S311. If there is a grid point not yet selected, then the visualization information generation section 120 performs step S306.

(Step S311) The visualization information generation section 120 generates an object of an isosurface on which potentials of voxels set in the pillar-shaped area are equal to the threshold. An isosurface is generated by connecting positions at which potential values are equal. For example, the visualization information generation section 120 obtains an isosurface by synthesizing a surface more distant from the sinoatrial node or the atrioventricular node by the use of voxels on an excitement propagation wave front generated on the basis of the threshold.

(Step S312) The rendering section 130 draws in the pillar-shaped area 62 an object of an isosurface indicative of an excitement propagation wave front for each time step. Furthermore, the rendering section 130 causes the monitor 21 to display an image obtained by the drawing. At this time the rendering section 130 causes the monitor 21 to display, for example, near an isosurface the number of a time step corresponding to the isosurface.

The position of an excitement propagation wave front for each time step is displayed in this way in a pillar-shaped area.

Figure 13:
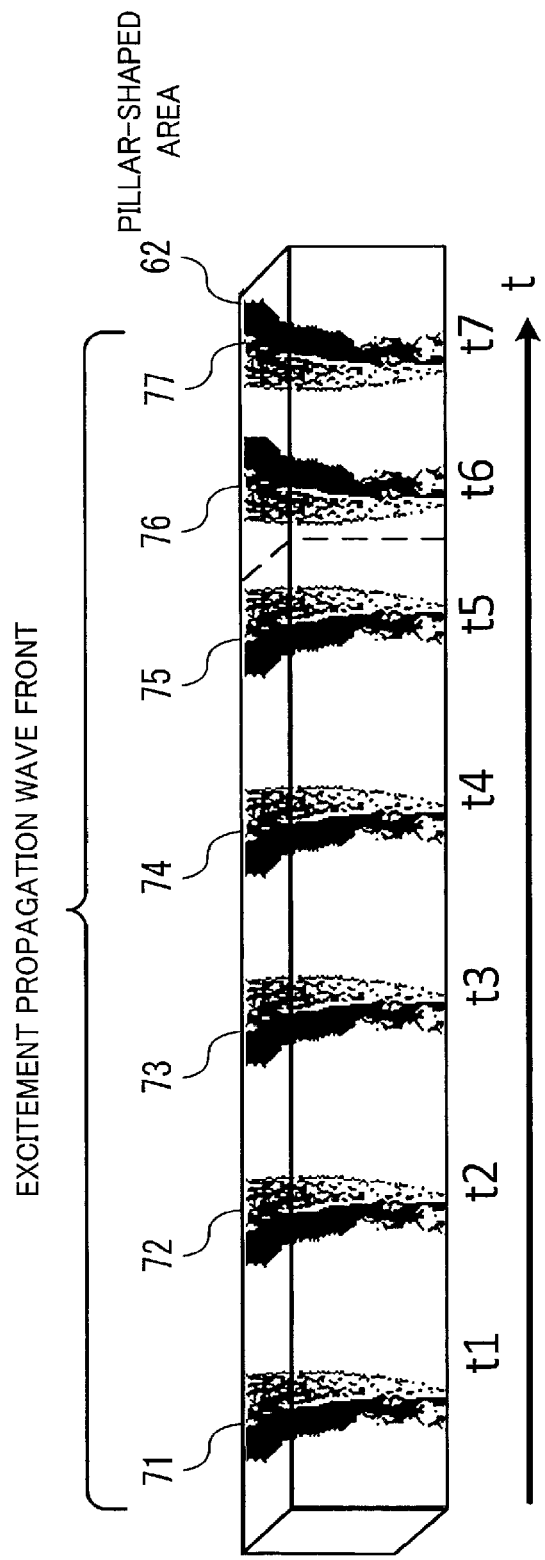
FIG. 13 illustrates an example of an excitement propagation wave front displayed in a pillar-shaped area.

FIG. 13 illustrates an example of an excitement propagation wave front displayed in a pillar-shaped area. Excitement propagation wave fronts 71 through 77 each of which is indicated by an isosurface for a time step are displayed in a pillar-shaped area 62. By displaying the excitement propagation wave fronts 71 through 77 in this way, how each excitement propagation wave front travels for one time step is easily grasped.

For example, the excitement propagation visualization apparatus 100 can display the state in which an excitement propagation wave front travels for a plurality of patients side by side. By doing so, the difference among the patients in the degree to which an excitement propagation wave front travels is easily grasped. In addition, the excitement propagation visualization apparatus 100 can display the state for a patient in which an excitement propagation wave front travels in the past (before treatment, for example) and the state for the patient in which an excitement propagation wave front travels at present (after treatment) side by side. As a result, a change in the condition of a disease of the patient is easily grasped.

Fourth Embodiment

Next, a fourth embodiment will be described. In a fourth embodiment, the state in which an excitement propagation wave front travels between two reference positions for one cycle of pulsation is displayed three-dimensionally in a ring-shaped area. The differences between the fourth embodiment and the third embodiment will now be described.

The visualization information generation section 120 generates in a pillar-shaped area an object indicative of the state in which an excitement propagation wave front travels. This is the same with the third embodiment. Furthermore, the visualization information generation section 120 transforms the pillar-shaped area into a ring-shaped area. By doing so, the visualization information generation section 120 displays in the ring-shaped area the object indicative of the state in which an excitement propagation wave front travels.

Next, a procedure for a visualization process in the fourth embodiment will be described in detail.

Figure 14:
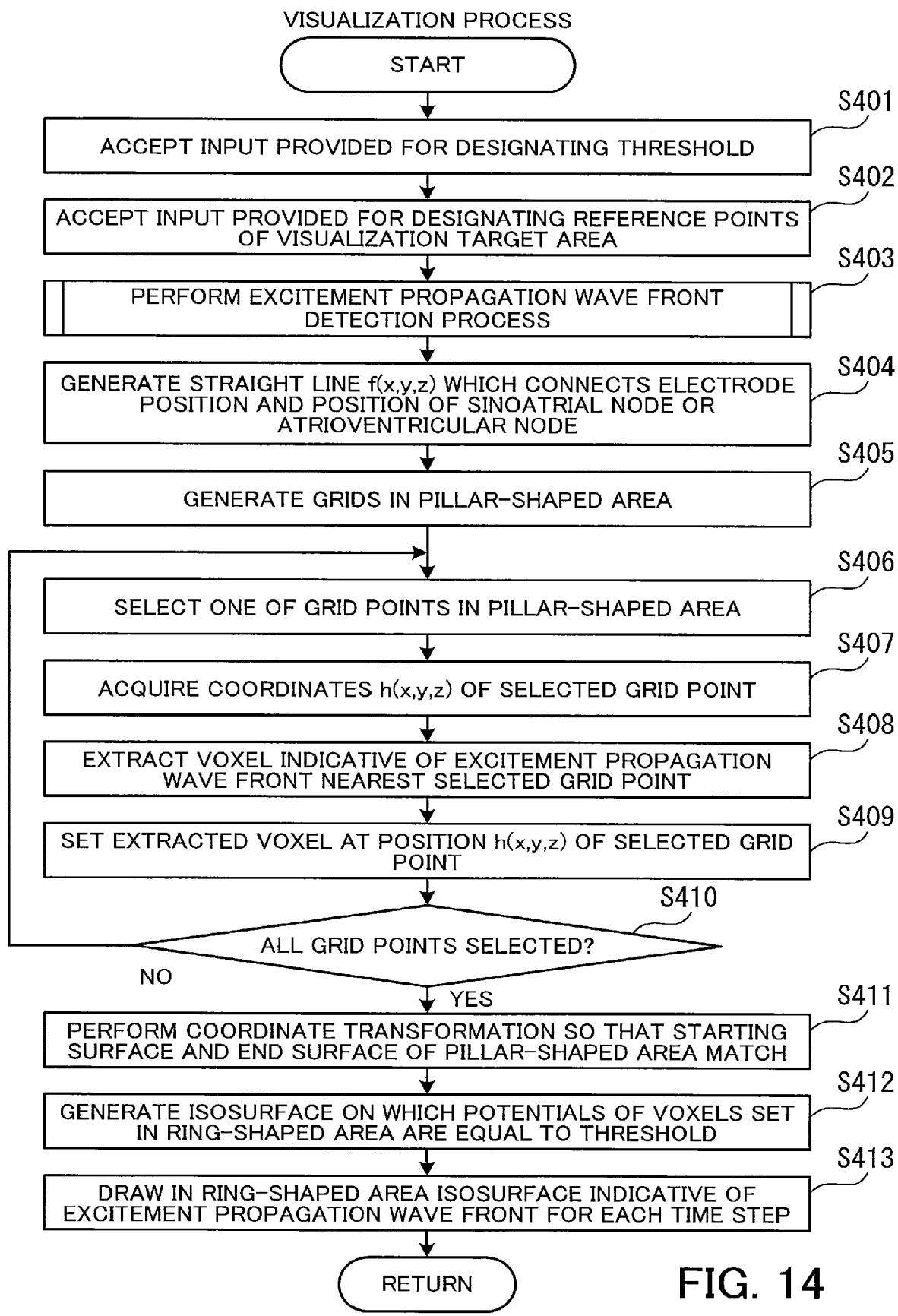
FIG. 14 is a flow chart illustrative of an example of a procedure for a visualization process in a fourth embodiment.

FIG. 14 is a flow chart illustrative of an example of a procedure for a visualization process in the fourth embodiment. Steps S401 through S410 are the same as steps S301 through S310, respectively, of the visualization process in the third embodiment illustrated in FIG. 12. Step S411 and the subsequent steps illustrated in FIG. 14 will now be described in order of step number.

(Step S411) The visualization information generation section 120 performs coordinate transformation so that a ring in which the starting surface (the starting position at which a time series of time steps starts) and the end surface (the end position at which the time series ends) of the pillar-shaped area match will be formed.

(Step S412) The visualization information generation section 120 generates an object of an isosurface on which potentials of voxels set in a ring-shaped area are equal to the threshold.

(Step S413) The rendering section 130 draws in the ring-shaped area an object of an isosurface indicative of an excitement propagation wave front for each time step. Furthermore, the rendering section 130 causes the monitor 21 to display an image obtained by the drawing. At this time the rendering section 130 causes the monitor 21 to display, for example, near an isosurface the number of a time step corresponding to the isosurface.

An excitement propagation wave front for each time step is displayed in this way in a ring-shaped area.

Figure 15:
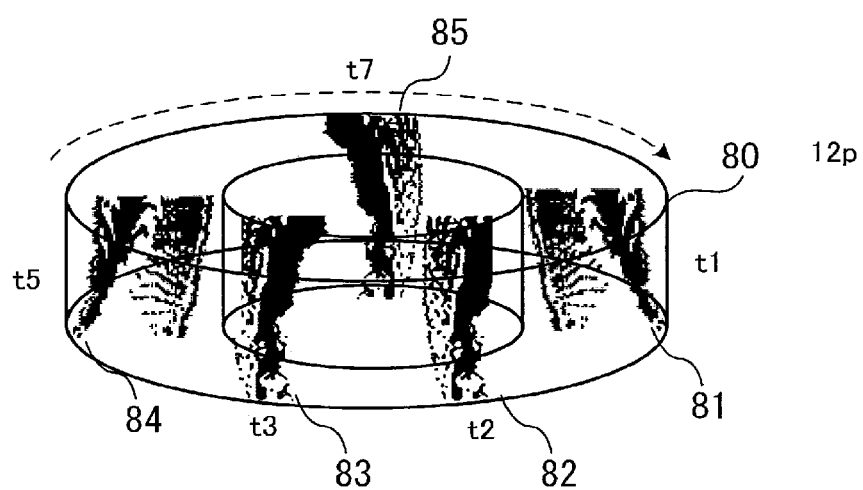
FIG. 15 illustrates an example of an excitement propagation wave front displayed in a ring-shaped area.

FIG. 15 illustrates an example of an excitement propagation wave front displayed in a ring-shaped area. Excitement propagation wave fronts 81 through 85 for individual time steps are displayed in a ring-shaped area 80. By displaying the excitement propagation wave fronts 81 through 85 in the ring-shaped area 80, the state of excitement propagation for one cycle of pulsation is easily grasped.

For example, ring-shaped areas indicative of the state of excitement propagation for a plurality of patients are displayed side by side. As a result, the difference in excitement propagation for one cycle of pulsation among the patients is easily found. Furthermore, a ring-shaped area indicative of the state of excitement propagation for a patient in the past (before treatment, for example) and a ring-shaped area indicative of the state of excitement propagation for the patient at present (after treatment) are displayed side by side. As a result, a change in excitement propagation for the patient for one cycle of pulsation is easily found.

Other Embodiments

In the first through fourth embodiments, an object of display for the state of excitement propagation is set between the sinoatrial node or the atrioventricular node and an electrode position for measuring an electrocardiogram. However, the object of display for the state of excitement propagation may be set in another range. For example, if a part with which a patient has trouble is known, then a user may set an object of display for the state of excitement propagation on a straight line passing through the part. In this case, the excitement propagation visualization apparatus 100 displays the state of excitement propagation in a range on the straight line passing through the part.

In addition, the excitement propagation visualization apparatus 100 may simultaneously display the state of excitement propagation for a plurality of parts. For example, a user designates a plurality of display target positions such as electrodes. In that case, the excitement propagation visualization apparatus 100 displays the state of excitement propagation from the sinoatrial node or the atrioventricular node to each of the plurality of display target positions. If the state of excitement propagation is displayed by the use of an arrow object, then the excitement propagation visualization apparatus 100 displays an arrow object indicative of the state of excitement propagation from the sinoatrial node or the atrioventricular node to each of the plurality of display target positions. At this time the excitement propagation visualization apparatus 100 superimposes the above arrow object on an image of the chest.

According to an aspect, the state of excitement propagation is plainly visualized.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various changes, substitutions, and alterations could be made hereto without departing from the spirit and scope of the invention.

What is claimed is:

1. An excitement propagation visualization apparatus comprising:
    a memory that stores excitement propagation data indicative of potentials generated by excitement propagation at a plurality of points in an analysis space including a heart at each analysis time in an analysis period; and
    a processor that executes a process including:
        detecting, based on the excitement propagation data and for the each analysis time, an excitement propagation wave front indicative of a boundary between an area in which the potentials exceed a threshold and an area in which the potentials do not exceed the threshold;
        detecting, for the each analysis time, an intersection of a straight line passing through a first point inside the heart and a second point outside the heart and the excitement propagation wave front;
        generating, for the each analysis time, a display object associated with the intersection of the straight line and the excitement propagation wave front; and
        drawing the display object generated for the each analysis time at a position of the associated intersection in a drawing area indicative of the analysis space,
    wherein, the generating includes generating a display object indicative of a portion of the excitement propagation wave front included in a pillar-shaped area surrounding the straight line; and
    wherein, the drawing includes drawing the display object for each analysis time in one pulsation period in a ring-shaped area obtained by transforming the pillar-shaped area.

2. An excitement propagation visualization method comprising:
    detecting, by a processor connected to a memory that stores excitement propagation data indicative of potentials generated by excitement propagation at a plurality of points in an analysis space including a heart at each analysis time in an analysis period, based on the excitement propagation data, and for the each analysis time, an excitement propagation wave front indicative of a boundary between an area in which the potentials exceed a threshold and an area in which the potentials do not exceed the threshold;
    detecting, by the processor and for the each analysis time, an intersection of a straight line passing through a first point inside the heart and a second point outside the heart and the excitement propagation wave front;
    generating, by the processor and for the each analysis time, a display object associated with the intersection of the straight line and the excitement propagation wave front; and
    drawing, by the processor, the display object generated for the each analysis time at a position of the associated intersection in a drawing area indicative of the analysis space,
    wherein, the generating includes generating a display object indicative of a portion of the excitement propagation wave front included in a pillar-shaped area surrounding the straight line; and
    wherein, the drawing includes drawing the display object for each analysis time in one pulsation period in a ring-shaped area obtained by transforming the pillar-shaped area.

3. A non-transitory computer-readable storage medium storing a program that causes a computer to execute a process comprising:
    detecting, based on excitement propagation data stored in a memory that is connected to the computer and for each analysis time, an excitement propagation wave front indicative of a boundary between an area in which potentials exceed a threshold and an area in which potentials do not exceed the threshold, the excitement propagation data being indicative of the potentials generated by excitement propagation at a plurality of points in an analysis space including a heart at each analysis time in an analysis period;
    detecting, for the each analysis time, an intersection of a straight line passing through a first point inside the heart and a second point outside the heart and the excitement propagation wave front;
    generating, for the each analysis time, a display object associated with the intersection of the straight line and the excitement propagation wave front; and
    drawing the display object generated for the each analysis time at a position of the associated intersection in a drawing area indicative of the analysis space,
    wherein, the generating includes generating a display object indicative of a portion of the excitement propagation wave front included in a pillar-shaped area surrounding the straight line; and
wherein, the drawing includes drawing the display object for each analysis time in one pulsation period in a ring-shaped area obtained by transforming the pillar-shaped area.

* * * * *